(12) United States Patent
Chen et al.

(10) Patent No.: US 8,764,666 B2
(45) Date of Patent: Jul. 1, 2014

(54) ULTRASOUND GUIDED OPTICAL COHERENCE TOMOGRAPHY, PHOTOACOUSTIC PROBE FOR BIOMEDICAL IMAGING

(75) Inventors: Zhongping Chen, Irvine, CA (US); Jiechen Yin, Irvine, CA (US); Qifa Zhou, Arcadia, CA (US); Changhong Hu, South Pasadena, CA (US); Hao-Chung Yang, Los Angeles, CA (US); Huihua Kenny Chiang, Aliso Viejo, CA (US); Kirk K. Shung, Monterey Park, CA (US)

(73) Assignee: The Regents of the University of California, Oakland, CA (US)

( * ) Notice: Subject to any disclaimer, the term of this patent is extended or adjusted under 35 U.S.C. 154(b) by 338 days.

(21) Appl. No.: 12/607,958

(22) Filed: Oct. 28, 2009

(65) Prior Publication Data
US 2011/0098572 A1 Apr. 28, 2011

Related U.S. Application Data

(60) Provisional application No. 61/109,146, filed on Oct. 28, 2008.

(51) Int. Cl.
*A61B 8/08* (2006.01)
*A61B 5/00* (2006.01)
*A61B 8/12* (2006.01)

(52) U.S. Cl.
CPC ............ *A61B 5/0066* (2013.01); *A61B 8/12* (2013.01)

USPC ................... 600/462; 600/459; 600/310

(58) Field of Classification Search
USPC ......... 600/310–342, 437, 440, 459–467, 473, 600/476–478
See application file for complete search history.

(56) References Cited

U.S. PATENT DOCUMENTS

| | | | |
|---|---|---|---|
| 5,718,231 A | 2/1998 | Dewhurst et al. | |
| 6,485,413 B1 * | 11/2002 | Boppart et al. | 600/160 |
| 2001/0007940 A1 * | 7/2001 | Tu et al. | 606/41 |
| 2004/0073120 A1 * | 4/2004 | Motz et al. | 600/478 |
| 2007/0066890 A1 * | 3/2007 | Maschke | 600/424 |

OTHER PUBLICATIONS

Kolkman et al. (Journal of Biomedical Optics, 9(6), 1327-1335, 2004).

* cited by examiner

*Primary Examiner* — Parikha Mehta
(74) *Attorney, Agent, or Firm* — Daniel L. Dawes; Marcus C. Dawes

(57) ABSTRACT

An imaging probe for a biological sample includes an OCT probe and an ultrasound probe combined with the OCT probe in an integral probe package capable of providing by a single scanning operation images from the OCT probe and ultrasound probe to simultaneously provide integrated optical coherence tomography (OCT) and ultrasound imaging of the same biological sample. A method to provide high resolution imaging of biomedical tissue includes the steps of finding an area of interest using the guidance of ultrasound imaging, and obtaining an OCT image and once the area of interest is identified where the combination of the two imaging modalities yields high resolution OCT and deep penetration depth ultrasound imaging.

15 Claims, 15 Drawing Sheets

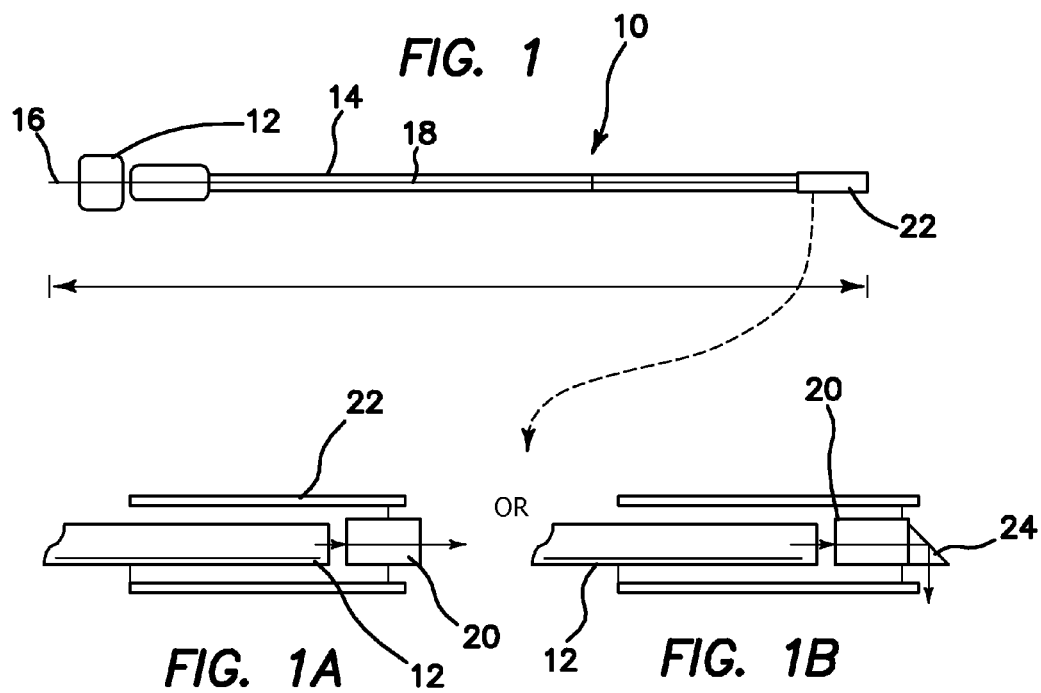
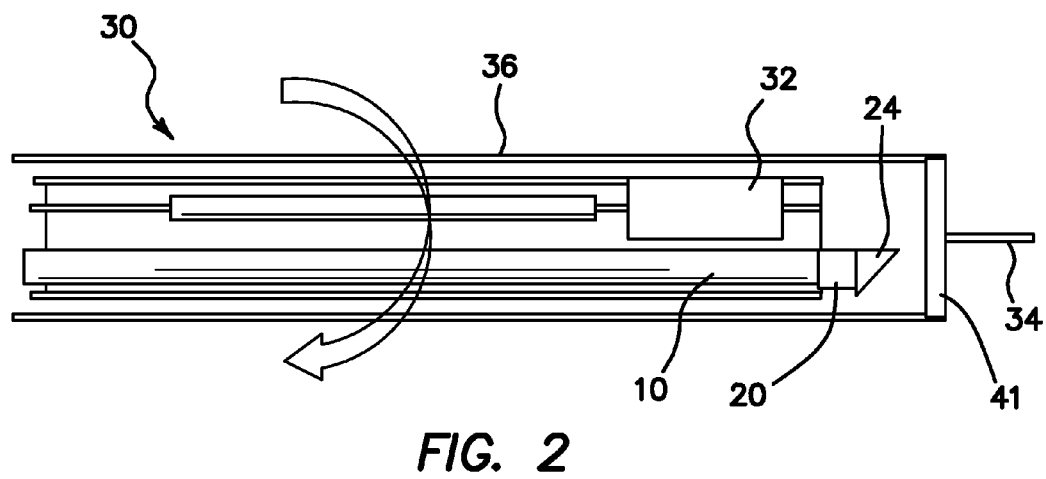

PROTOTYPE 6

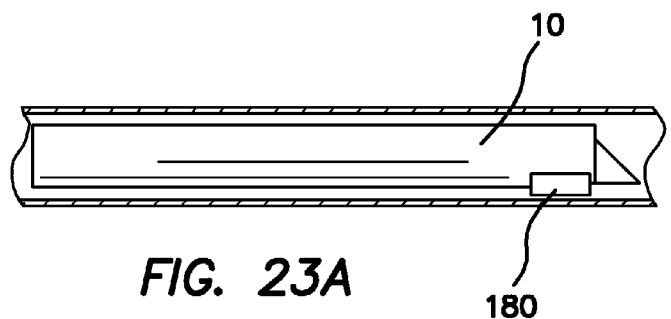 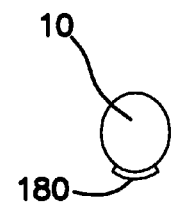
FIG. 23A          FIG. 23B
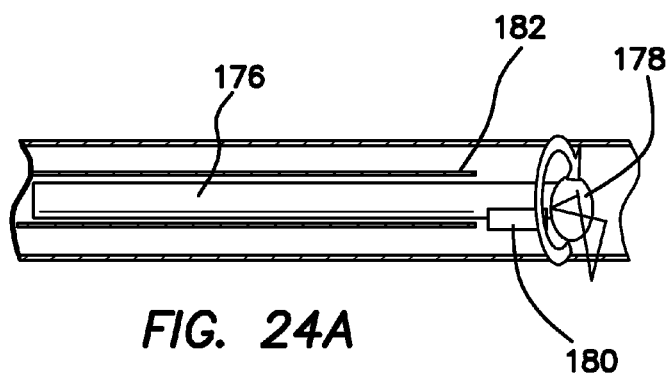 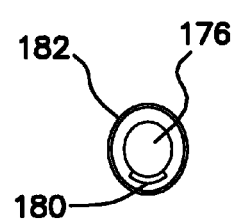
FIG. 24A          FIG. 24B
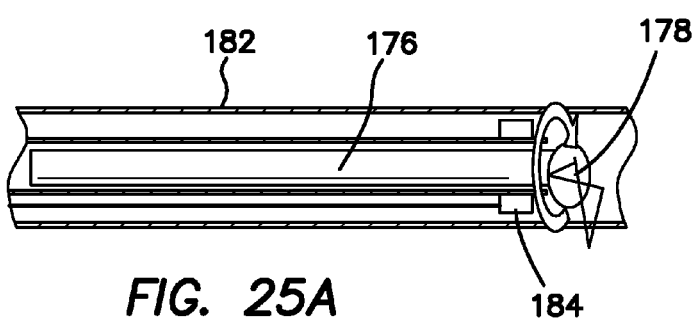 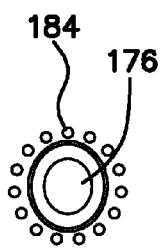
FIG. 25A          FIG. 25B

ULTRASOUND GUIDED OPTICAL COHERENCE TOMOGRAPHY, PHOTOACOUSTIC PROBE FOR BIOMEDICAL IMAGING

RELATED APPLICATIONS

The present application is related to U.S. Provisional patent application Ser. No. 61/109,146, filed on Oct. 28, 2008, which is incorporated herein by reference and to which priority is claimed pursuant to 35 USC 119.

GOVERNMENT SUPPORT

This invention was made with government support under Contract Nos. EB000293 and P41 EB002182 awarded by the National Institutes of Health. The government has certain rights in the invention.

BACKGROUND OF THE INVENTION

1. Field of the Invention

The invention relates to the field of intravascular imaging, in particular to an integrated ultrasound guided optical coherence tomography, photoacoustic probe used in intravascular or biomedical imaging and a method of using the same.

2. Description of the Prior Art

Intravascular ultrasound (IVUS) is a medical imaging methodology that has been used to show the anatomy of the wall of blood vessels in living animals and humans by using a miniaturized ultrasound probe. IVUS can help physicians determine the amount of plaque from the cross-sectional image of blood vessels. In other words, IVUS can visualize not only the lumen of the coronary arteries but also the objects hidden within the wall, such as atheroma. However, because the reflection coefficient of the ultrasound of blood vessel is quite small, high sensitivity and larger bandwidth ultrasound probe are key factors of high-quality intravascular ultrasound images. High sensitivity and large bandwidth probes can be fabricated by using high electromechanical coupling coefficient ($K_t$) piezoelectric materials. Research shows $Pb(Mg_{1/3}Nb_{2/3})O_3$—$PbTiO_3$ (PMN-PT) is the one of the most promising high $K_t$ commercial piezoelectric materials. It has been reported that a PMN-PT may be used as a single crystal transducer with a −6 dB fractional bandwidth of 114%.

On the other hand, the outer diameter of the ultrasound probe should be less than 3 mm to fulfill the requirement of IVUS biomedical imaging applications. Therefore, the fabrication of a miniaturized ultrasound probe is another important issue for IVUS imaging. High frequency (40 MHz) PMN-PT needle ultrasound transducers for biomedical applications have been made known in the art.

Optical coherence tomography (OCT) is a recently developed imaging modality using coherent gating to obtain high-resolution surface images of tissue microstructure. OCT endoscope design uses a fixed gradient-index (GRIN) lens and prism as the optical tip. Rotational torque is transferred from the endoscope's proximal end to the distal tip. OCT can provide imaging resolutions that approach those of conventional histopathology and can be performed in situ and in vivo. In vivo images of living animals have been demonstrated by using motor-based scanning endoscopic probes known in the art.

Nevertheless, one of drawbacks of OCT is that it needs to use saline water to flush blood away from the probe in order to remove the interference received from the blood. Therefore, how to minimize the times of saline water flushing is becoming a major topic in the OCT research filed nowadays. This problem is currently solved by inserting a balloon catheter at the imaging region to achieve blood occlusion, or by injecting relative large amounts of saline or other agents to flush away blood. However, both solutions have medical safety concerns. In the case of IVUS imaging, blood serves as the natural transmission media of the sound wave.

Additionally, the imaging resolution of IVUS is much less than that of OCT. In particular, IVUS is able to visualize the coronary artery from the inside-out owing to its larger penetration depth than OCT. In direct contrast, OCT can provide high-quality, micrometer-resolution, and three-dimensional images which are superior to IVUS.

Therefore, what is needed is a novel imaging probe combining a high frequency IVUS transducer with a 3-D scanning OCT probe to obtain the high-resolution cross-sectional intravascular images.

Optical coherent tomography (OCT) and ultrasound imaging are two of the most widely used image modalities. These image modalities share with common advantages, including: low-cost, high spatial resolution, portable, real-time, noninvasive, and non-radioactive. OCT and ultrasound imaging both measure cross-sectional tissue image. OCT measures tissue surface profile and cross-sectional image within a few millimeter depth range under the skin with a superior image resolution of 10 micrometers; high frequency ultrasound imaging also measures cross-sectional tissue image with a much deeper depth but with lower image resolution, on the order of 100 micrometers. OCT and ultrasound imaging modalities can be combined to provide a deeper cross-sectional imaging (tomography).

However, conventional ultrasound imaging performs relatively poor in blood vessel imaging, with lower imaging contrast, due to weak echo-genicity of blood. With recent developments in photoacoustics imaging, this limitation can be resolved. Photoacoustics imaging exploits the selective absorption property of hemoglobin to visible and near infrared (500-1200 nm) radiation, while tissues are relatively transparent in this optical spectrum. Through the optical absorption and thermoelastic expansion of blood vessels to short laser pulses, broadband ultrasound echo signals, up to 40 MHz, are generated from nanosecond laser radiated blood vessels. Since photoacoustic signals share the same acoustic spectra with ultrasound, photoacoustics imaging can be acquired and reconstructed by conventional ultrasound system.

A paper, entitled "Photoacoustic imaging of blood vessels with a double-ring sensor featuring a narrow angular aperture" by Kolkman et al. (Journal of Biomedical Optics, 9(6), 1327-1335, 2004) has proposed the development of a photoacoustic imaging probe, consisting of a double-ring polyvinylidene fluoride (PVDF) piezoelectric polymer sensor and an optical fiber located at its center. A 600 micrometer diameter optical fiber is used to transmit near infrared light to excite blood vessels; the double-ring piezoelectric polymer sensors acquire acoustic signal to generate ultrasound image.

U.S. Pat. No. 5,718,231, entitled "Laser ultrasound probe and ablator" describes a laser ultrasound probe, consisting of a ultrasound receiving sensor, made of PVDF piezoelectric polymer material for receiving photoacoustic signals and an optical fiber for transmitting laser radiation and generating photoacoustic signals by radiating the laser onto blood vessels.

Both of the above related prior art documents fail to present the concept of integrating OCT/ultrasound imaging/photoacoustics imaging modalities into a single image probe.

BRIEF SUMMARY OF THE INVENTION

The illustrated embodiment of the disclosure covers an imaging probe which integrates optical coherence tomography (OCT) and ultrasound imaging. Ultrasound guided optical coherence tomography (ultra-OCT) is a new imaging modality that integrates optical coherence tomography with ultra sound imaging.

A hollow-core ultrasound transducer is provided with the optical tip of an OCT probe inserted into its core. The optical tip of the OCT probe includes an 8 degree cut single mode fiber and a GRIN lens. The OCT probe is combined with an ultrasound transducer. A focused light beam together with ultrasound wave are reflected by a prism, and the focal point of the light is in tissue.

The purpose of this system is to provide a means for high resolution imaging of biomedical tissue. The guidance of ultrasound imaging allows the area of interest to be found and thus a relatively smaller amount of flush agent will be needed, which provides a safer way to obtain intravascular OCT images. The combination of the two imaging modalities yields high resolution thanks to OCT and deep penetration depth due to ultrasound imaging.

The Ultra-OCT probe uses its ultrasound modality to acquire images and search along inside of the vessel first. When finding area of interest, a small amount of flushing agent is applied to create an imaging window for OCT. No blood occlusion is needed, and a smaller amount of flushing is required, thus ultrasound guided OCT is potentially safer than conventional intravascular OCT, and it provides much higher resolution than intravascular ultrasound (IVUS).

The invention will be used to develop a clinically useful endoscopic Ultra-OCT system that can provide high resolution optical imaging of internal organs and tissues such as vessels. OCT can provide high resolution cross sectional imaging that conventional endoscopy cannot. At the same time, a reduced dose of flush agent will be needed using this invention compared with conventional OCT imaging system. The current invention allows OCT to be used potentially anywhere that can be accessed by endoscopy. Examples of use include but are not limited to intravascular catheter vessel imaging, bladder cancer detection and other aspects in the field of urology, lung cancer detection and inflammation and other aspects in pulmonary medicine, arterial anastomosis other minimally invasive surgeries, cardiac cancer detection, gynecological diagnosis of endometriosis and cancer, and cancer and inflammation detection in the gastrointestinal tract.

Other functions can also be added to this invention to give arise to multiple applications; polarization sensitive OCT can offer the information on light polarization changing properties of tissue; Doppler OCT can yield quantification of blood flow velocity; imaging guided therapy can also be achieved by adding an therapeutic channel to the probe, etc. Any OCT modality now known or later devised can be employed in the combination.

Further, an integrated biomedical multimodality image probe is disclosed which combines OCT, ultrasound imaging, and photoacoustics imaging to provide morphological as well as function imaging of tissues and blood vessels with a high spatial resolution and imaging contrast. The image probe acquires image on its front or on its side. The image probe is moved in a linear scan mode or a helical scan mode by linear translation stage and microelectromechanical system (MEMS) motor to acquire and construct 2D or 3D cross-sectional tissue images.

This embodiment of the illustrated invention includes an integrated biomedical multimodality image probe that combines three different image modalities: OCT, high frequency ultrasound imaging, and photoacoustics imaging, all together into a portable image probe. Cross-sectional images of tissue on the front or on the side of the probe can be obtained by these three image modalities. The multimodality imaging probe combines OCT, ultrasound imaging, and photoacoustics imaging components into an integrated system that measures cross-sectional images of tissue on the front or on the side of the probe. OCT measures tissue surface profile and cross-sectional tissue and blood vessel image within 1 mm range with superior image resolution, high frequency ultrasound imaging also measures tissue cross-sectional image with superior image depth but with inferior image resolution.

In addition, photoacoustics imaging and ultrasound imaging share with the same imaging system on the receiving side, photoacoustics imaging measures blood vessel image with superior image contrast than conventional ultrasound imaging. Therefore, these image modalities are ready to be integrated, and the new image can be shown in one image format. By combining these image modalities into an integrated image probe, it can image high resolution tissue image by OCT and ultrasound imaging and high contrast blood vessel image and functional imaging by photoacoustics imaging. In addition, it provides an integration of OCT and ultrasound imaging that covers from tissue surface profiles to 1 cm below the skin. It can be used for clinical imaging applications, including tissue physiological (oxi-hemoglobin/deoxi-hemoglobin) parameter monitoring, blood vessel measurements, or early tumor and dysplasia monitoring.

The purpose of this embodiment is to provide a noninvasive and portable image probe that provides superior images resolution, contrast, and depth of image on real-time basis. This multimodality image probe can provide 10-100 micrometers image resolution for tissue and blood vessel cross-sectional image within 1 cm depth range.

An OCT image is obtained by transmitting/receiving visible or near-infrared laser light to acquire tissue surface profile and cross-sectional tissue and blood vessel images. Ultrasound imaging and OCT are very similar in imaging principle; ultrasound imaging is formed by sending and receiving ultrasound waves. Although, photoacoustics imaging requires sending nano-second visible/near infrared laser pulses to excite blood vessels and generate photoacoustic pressure waves. However, photoacoustics imaging measures the thermoelastic pressure waves generated from the blood vessels, and these pressure waves can be received and constructed by ultrasound imaging using the same ultrasound imaging system. Therefore, the ultrasound transducer can be used for acquiring a traditional Ultrasound tissue image and a photoacoustic image. These images are ready to be superimposed and integrated to form a new type of data image. Traditional OCT image is limited to a shallow imaging depth, near 1 mm. In addition, ultrasound imaging also has limitation in achieving high image contrast for blood vessels. By combining OCT, ultrasound imaging and photoacoustics imaging image modalities into an integrated image probe, it provides tissue and blood vessel cross-sectional image with a deeper depth of image.

In addition, it is worth noting that the integration of the OCT, ultrasound imaging and photoacoustics imaging does not further complicate the structure of the image probe head. Ultrasound imaging and photoacoustics imaging shares the same ultrasound transducer.

There is no exact prior device known for direct comparison to the integrated probe of the illustrated embodiment. The combined OCT, ultrasound imaging and photoacoustics imaging probe has superior imaging capability over each of the individual image modalities. It has superior image resolution to ultrasound imaging with a resolution within 1 mm by using OCT; it covers a deeper imaging depth than OCT by using ultrasound imaging; it has higher blood vessel contrast than ultrasound imaging by using photoacoustics imaging.

Thus, in summary the illustrated embodiment of the invention is an imaging probe for a biological sample which includes an OCT probe and an ultrasound probe combined with the OCT probe in an integral probe package capable of providing by a single scanning operation images from the OCT probe and ultrasound probe to simultaneously provide integrated optical coherence tomography (OCT) and ultrasound imaging of the same biological sample.

In one embodiment the OCT probe may include an optical fiber coupled to a GRIN lens adapted for forward scanning and the ultrasound probe may include a needle intravascular ultrasound (IVUS) transducer with a flat distal end adapted for forward scanning.

In another embodiment the OCT probe includes an optical fiber coupled to a GRIN lens and a prism reflector adapted for side scanning and the ultrasound probe includes an angled distal end adapted for side scanning.

In still another embodiment the OCT probe includes an optical fiber coupled to a GRIN lens and a mirror/reflector optically coupled thereto adapted in combination for side scanning and where the ultrasound probe includes a needle intravascular ultrasound (IVUS) transducer sonically coupled to the mirror/reflector adapted in combination for side scanning.

In yet another embodiment the OCT probe includes an optical fiber coupled to a GRIN lens and a mirror/reflector optically coupled thereto adapted in combination for side scanning and the ultrasound probe includes a ring-type intravascular ultrasound (IVUS) transducer sonically coupled to the mirror/reflector adapted in combination for side scanning, wherein the OCT probe is disposed longitudinally through the ring-type intravascular ultrasound (IVUS) transducer.

The imaging probe may further include a motor coupled to the mirror reflector for selectively rotating the mirror/reflector relative to the OCT probe and ultrasound probe.

In one illustrated embodiment the OCT probe includes an optical fiber coupled to a GRIN lens and a prism reflector adapted for side scanning and where the ultrasound probe includes an annular linear array ultrasound transducer adapted for side scanning with dynamic depth focusing.

In still another illustrated embodiment the OCT probe includes an optical fiber coupled to a GRIN lens adapted for forward scanning and where the ultrasound probe includes a ring-type intravascular ultrasound (IVUS) transducer adapted for forward scanning, wherein the OCT probe is disposed longitudinally through the ring-type intravascular ultrasound (IVUS) transducer.

The optical fiber in some of the illustrated embodiments includes an 8 degree cut single mode fiber.

The illustrated embodiment of the imaging probe further includes a device for linearly moving the OCT probe and ultrasound probe together and/or a device for rotating the OCT probe and ultrasound probe together.

The illustrated embodiment of the invention also includes within its scope a method to provide high resolution imaging of biomedical tissue comprising the steps of finding an area of interest using the guidance of ultrasound imaging and applying a reduced amount of flush agent to obtain an OCT image and once the area of interest is identified as compared to the amount of flush that would used if the area of interest was not first identified, where the combination of the two imaging modalities yields high resolution OCT and deep penetration depth ultrasound imaging.

More generally, the illustrated embodiment includes a method to provide high resolution imaging of biomedical tissue including the steps of finding an area of interest using the guidance of ultrasound imaging, and obtaining an OCT image and once the area of interest is identified where the combination of the two imaging modalities yields high resolution OCT and deep penetration depth ultrasound imaging.

The method further includes the step of using an ultra-OCT probe in its ultrasound modality to acquire images and search along inside of the vessel first, and when finding area of interest, applying a reduced amount of flushing agent to create an imaging window for OCT without occluding blood flow, and whereby a smaller amount of flushing is required than in conventionally used in OCT endovascular imaging, so that ultrasound guided OCT is safer than conventional intravascular OCT, while providing higher resolution than intravascular ultrasound (IVUS).

The steps of finding an area of interest using the guidance of ultrasound imaging and applying a reduced amount of flush agent to obtain intravascular OCT images is employed in a procedure related to intravascular catheter vessel imaging, urology-bladder cancer detection, pulmonary medicine, lung cancer detection and inflammation, surgery/minimally invasive surgery, arterial anastomosis, cancer detection, gynecological diagnosis including endometriosis or cancer, or gastrointestinal cancer and inflammation detection.

The method further includes within its scope using polarization sensitive OCT, Doppler OCT, or imaging guided therapy using a therapeutic channel to the probe.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1 is a side plan view of an OCT probe according to the invention.

FIG. 1a is a side cross-sectional view of one embodiment of the OCT probe of FIG. 1 in enlarged scale showing the distal tip portion.

FIG. 1b is a side cross-sectional view of another embodiment of the OCT probe of FIG. 1 in enlarged scale showing the distal tip portion.

FIG. 2 is a side cross-sectional view of a first embodiment of the ultra-OCT imaging probe of the illustrated embodiments using a needle IVUS ultrasound probe and the OCT probe of FIG. 1.

FIG. 3b is an end plan view of the needle ultrasound transducer of FIG. 3a.

FIG. 6b is an end plan view of the ring-type IVUS ultrasound probe of FIG. 6a.

FIG. 10b is a plan end view of the ultra-OCT imaging probe of FIG. 10a.

FIGS. 23a and 23b illustrate diagrammatic side cross-sectional view of the side and end view of an OCT probe with a distal membrane ultrasound transducer.

FIGS. 24a and 24b illustrate diagrammatic side cross-sectional view of the side and end view of a lensed optical fiber OCT probe with a ball lens with a distal membrane ultrasound transducer.

FIGS. 25a and 25b illustrate diagrammatic side cross-sectional view of the side and end view of a lensed optical fiber OCT probe with a ball lens with a distal membrane ultrasound transducer array.

Figure 3A:
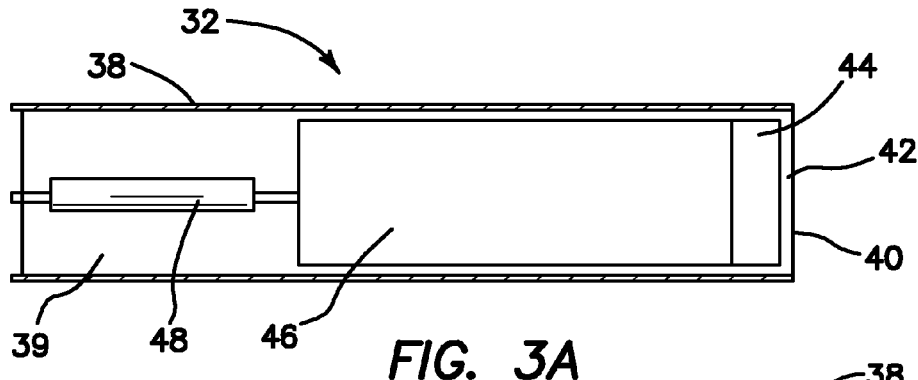
FIG. 3a is a side cross-sectional view of a first embodiment of the needle ultrasound transducer.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

An optical coherence tomography (OCT) probe is shown in the side plan view of FIG. 1 and is generally represented by reference numeral 10. A single mode optical fiber 12 is used to transmit light from a light source to biomedical sample or target (both not shown). Any type of light source used or usable in optical coherence tomography may be employed. The single mode fiber 12 is protected by a steel tube 14, which helps increase the stiffness of the proximal portion of the fiber 12 that is near an adaptor 16 where mechanical rotation is introduced. A flexible coil wire 18 is disposed through and beyond the distal end of the steel tube 14 to give flexibility to the distal tip of the probe 10 contained within a polyimide tube 22. Light from the distal tip of the single mode fiber 12, which may be an angle polished fiber, is focused by a gradient-index (GRIN) lens 20 into a focusing point in or on the target tissue as seen in FIGS. 1a and 1b. FIG. 1a is a side cross-sectional view of a first embodiment of the distal end of the polyimide tube 22 in enlarged scale showing a first embodiment employing GRIN lens 20 to provide a longitudinal beam, while FIG. 1b is a side cross-sectional view of a second embodiment of the distal end of the polyimide tube 22 in enlarged scale showing a second embodiment employing GRIN lens 20 and optically coupled prism 24 to provide a side beam. The focal length of the beam can be adjusted from 0 to 5 mm by changing the distance between the fiber 12 and the GRIN lens 20 during assembly of the probe 10.

As shown in FIG. 1b the OCT probe 10 may be used to focus light into tissue to the side of the probe 10 by means of employing a prism 24 disposed after the GRIN lens 20. The prism 20 is coupled to the GRIN lens 20 to reflect the light beam perpendicular to its incident or longitudinal direction. In cases where only forward scanning is needed, the prism 20 will not be necessary.

FIG. 2 shows in side cross-sectional view a first embodiment of the current invention as a combination of a needle intravascular ultrasound (IVUS) transducer 32 and the OCT probe 10 to form an ultra-OCT probe 30. Both the ultrasound transducer 32 and OCT probe 10 are contained within an elongate housing 36 comprised of fluorinated ethylene propylene (Teflon-FEP, or FEP) tubing or other similar material known in the art. In this particular embodiment, the ultrasound transducer 32 is disposed above the OCT probe 10 within the housing 36. The ultrasound waves produced by ultrasound transducer 32 and the light beam produced by the OCT probe 10 propagate perpendicular to the longitudinal axis of the ultra-OCT probe 30. A conventional guide wire 34 is coupled to the distal tip of the ultra-OCT probe 30 in the intravascular imaging application. The outside diameter of the ultra-OCT probe 30 is less than 3 mm. The ultra-OCT probe 30 may be used for rotational scanning by mechanically rotating the ultra-OCT probe 30 around the longitudinal axis of housing 36 as shown in FIG. 2. In the case of linear scanning, only transverse motion of housing 36 is performed.

Figure 3B:
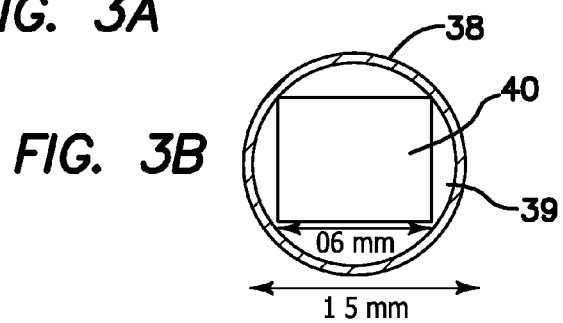
Figure 4:
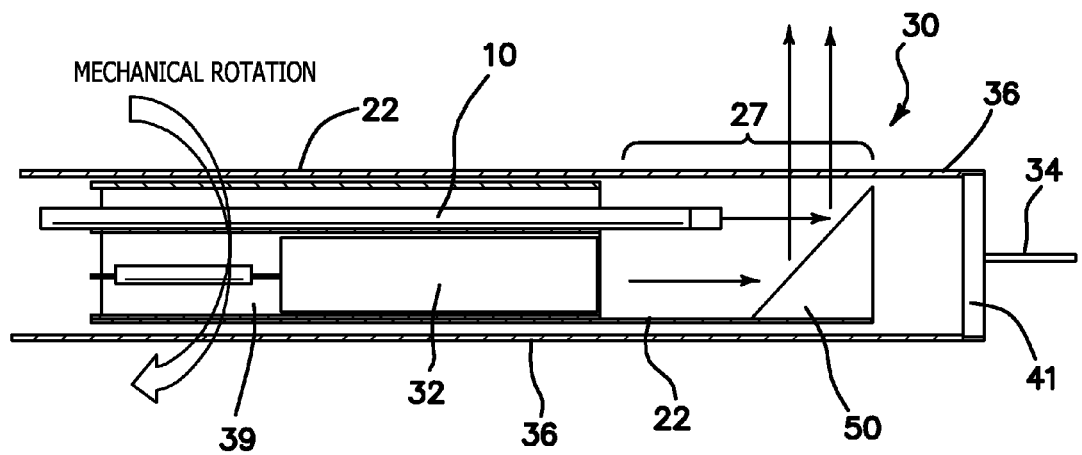
FIG. 4 is a side cross-sectional view of a second embodiment of the ultra-OCT imaging probe of the illustrated embodiments using a needle IVUS ultrasound probe using a mirror/reflector and the OCT probe of FIG. 1.
Figure 5:
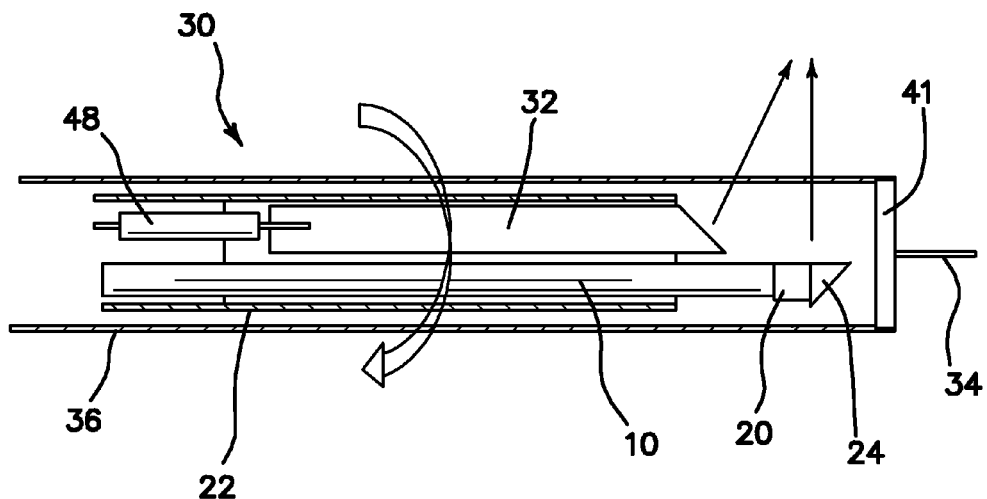
FIG. 5 is a side cross-sectional view of a second embodiment of the ultra-OCT imaging probe of the illustrated embodiments using an angled needle IVUS ultrasound probe and the OCT probe of FIG. 1.

Another embodiment of ultrasound transducer 32 can be seen in FIGS. 3a, and 3b and combined with an OCT probe 10 in FIG. 4. The ultrasound transducer 32 of FIGS. 3a, 3b comprises a stainless steel housing 38. At the distal tip of the housing 38 is a gold conduction layer 40. Proximally disposed to the gold conduction layer 40 is a first matching layer 42 and a piezoelectric layer 44. Proximally adjacent to the piezoelectric layer 44 is a backing 46. Coupled to the proximal end of the backing 46 is a wire 48 that extends to the proximal end of the ultra-OCT probe 30. The wire 48, backing 46, PMN-PT 44, and matching layer 42 are embedded or potted within the distal portion of housing 38 in an epoxy 39.

The piezoelectric layer 44 preferably has a sufficiently high coupling coefficient $K_t$. High $K_t$, one the most important parameters in ultrasound transducer applications, allows for higher sensitivity and larger bandwidth for the small aperture ultrasound transducers, such as for a needle single element ultrasound transducer 32 seen in FIG. 3a. A Pb(Mg$_{1/3}$Nb$_{2/3}$)O$_3$—PbTiO$_3$ (PMN-PT) ($K_t$=0.58, HC Materials Corp., Urbana, Ill.) single crystal is preferably used as the piezoelectric transducing material 44 of the high frequency ultrasonic needle transducer 32. The needle ultrasound transducer 32 was designed using a commercial transducer modeling software PiezoCAD (Woodinville, Wash.) to optimize its performance. The center frequency of the ultrasound needle transducer 32 was designed at 35 MHz as a trade-off between resolution and penetration depth. The aperture size of the ultrasound transducer 32, which has a square cross-section as shown in the end plan view of FIG. 3b, is diced to 0.6 mm×0.6 mm in$^2$ to match electrical impedance (50 ohms). The outside diameter of the needle ultrasound transducer 32 is 1.5 mm as seen in the cross-sectional drawing of the needle ultrasound transducer 32 of FIG. 3b.

The needle ultrasound transducer 32 of FIG. 3a is combined with an OCT probe 10 of the type described above in connection with FIG. 1, both of which are similarly embedded or potted in an epoxy filled distal portion of polyimide tube 22 as shown in FIG. 4. The longitudinal light beam and ultrasound beam are directed to a corner optical mirror and sound reflector 50 mounted at the distal end of tube 22 to reflect the light beam and ultrasound beam through an open window 27 defined in tube 22 as side beams. In FIG. 4, an alternative embodiment of the ultra-OCT probe 30 is shown where the OCT probe 10 is disposed above or in combination with the ultrasound transducer 32 within the polyimide tube 22. The OCT probe 10 uses a fixed gradient-index (GRIN) lens 20 as the optical tip. The 1310 nm single mode fiber 12 within the OCT probe 10 was cut to 8 degrees and glued to a focusing GRIN lens 20. A 2 mm diameter prism with aluminum coating (Edmund Optics, Barrington, N.J.) was used as mirror 50 to reflect the ultrasound beams from the ultrasound transducer 32 and the light beams form the OCT probe 10 from the forward direction to a substantially side direction. Tube 22 is in turn disposed within FEP housing 36, which may be capped at its distal end with an distal guidewire 34 attached by medical glue 41 to facilitate endovascular applications. The entire ultra-OCT probe 30 diameter of FIG. 4 is approximately 3 mm or less. Like the previous embodiment, mechanical rotation in the direction indicated in FIG. 4 is required in order to achieve rotational scanning.

Figure 6A:
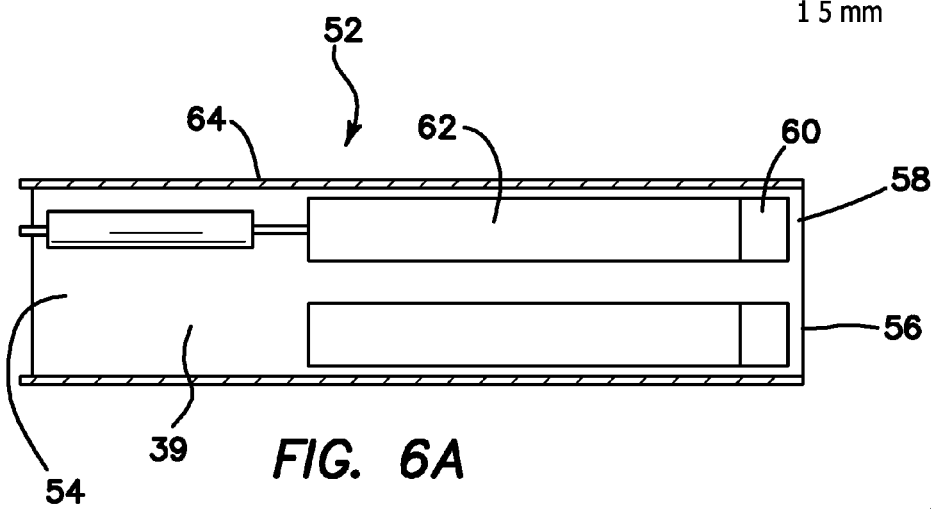
FIG. 6a is a side cross-sectional view of a ring-type IVUS ultrasound probe.
Figure 6B:
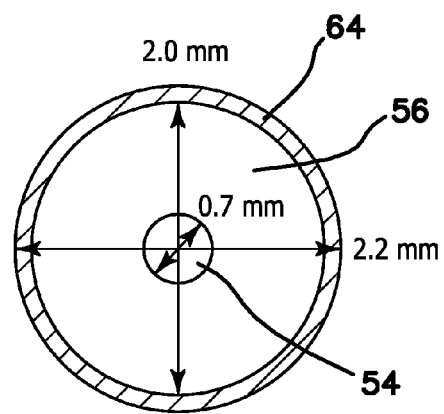
Figure 7:
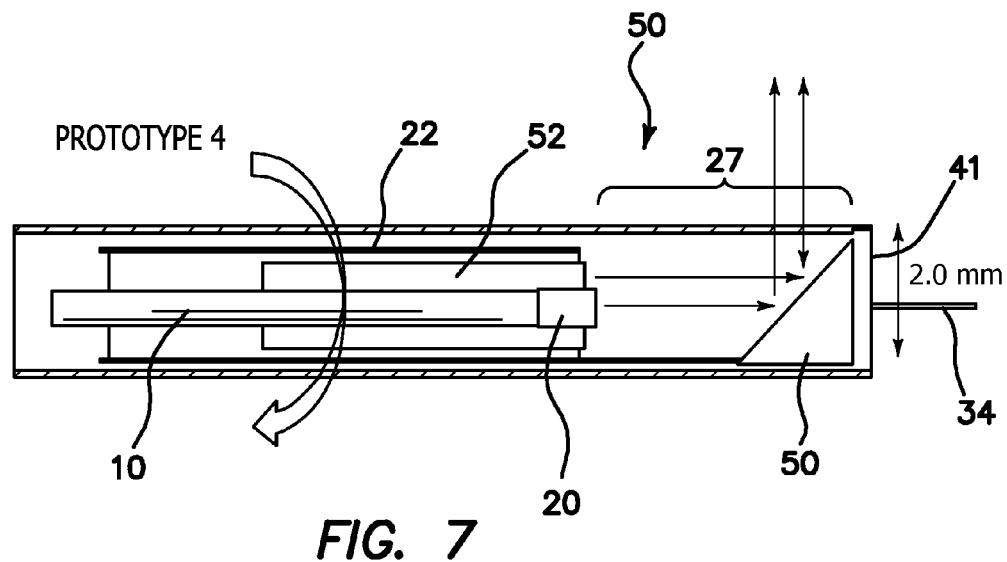
FIG. 7 is a side cross-sectional view of a third embodiment of the ultra-OCT imaging probe of the illustrated embodiments using a ring-type IVUS ultrasound probe of FIGS. 6a and 6b and the OCT probe of FIG. 1.

In a further embodiment depicted in FIGS. 6a, 6b and 7, a ring type ultrasound transducer 52 is employed within the ultra-OCT probe 30. A side cross-sectional view of the ring ultrasound transducer 52 is seen in FIG. 6a. Like the ultrasound transducer 32 disclosed above, the ring ultrasound transducer 52 comprises a gold conduction layer 56 at its most distal tip, followed proximally by a first matching layer 58, a piezoelectric layer 60, and a backing layer 62 in that order and all embedded or potted in an epoxy fill 39 contained within an elongate stainless steel housing 64. Wire 48 extends from the backing layer 62 to the proximal end of the ultra-OCT probe 30. However defined through the entire longitudinal length of the ring ultrasound transducer 52 is an inner axial longitudinal cavity 54. The inner cavity 54 is substantially cylindrical in shape and is defined through the center of the ring ultrasound transducer 52 as seen in the end plan view of FIG. 6b. The OCT probe 10 is then disposed through cavity 54.

The combination of the ring ultrasound transducer 52 with OCT probe 10 into the ultra-OCT probe 30 is seen in the side cross-sectional view of FIG. 7. The OCT probe 10, including the GRIN lens 20, is disposed within the inner cavity 54 of the ring ultrasound transducer 52. The combined ring ultrasound transducer 52 with OCT probe 10 are disposed, embedded or potted within FEP tube 22 and combined with mirror/reflector 50 mounted at the distal end of tube 22. Light from the OCT probe 10 that is surrounded by ultrasound from the ring ultrasound transducer 52 is then sent forward to the mirror/reflector 50 to reflect the incoming light and sound beams perpendicularly to the incident longitudinal direction through FEP tubing 22. In this configuration, the ultrasound and light beams can be focused on a small region of target tissue at the same time. Again probe 30 may be capped at its distal end with medical glue 41 and provided with a guidewire 34.

Figure 8:
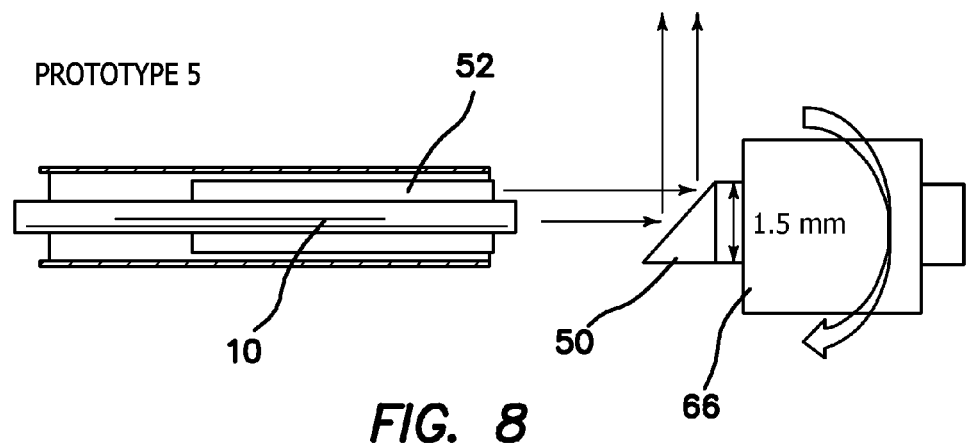
FIG. 8 is a side cross-sectional view of a fourth embodiment of the ultra-OCT imaging probe of the illustrated embodiments using a ring-type IVUS ultrasound probe of FIGS. 6a and 6b and the OCT probe of FIG. 1 using a MEMS motor.

Another embodiment of probe 30 is made with a ring type ultrasound transducer 52, an OCT probe 10 as described above in connection with FIGS. 6a, 6b and 7 and a MEMS motor 66 as schematically depicted in cross-sectional side view in FIG. 8. The OCT probe 10 is inserted into the center hole 54 of ring type ultrasound transducer 52. A mirror/prism 50 is mounted at a shaft of the MEMS motor 66 at an angular position of 45° relative to the longitudinal axis of rotation to allow selective change the propagation direction of the ultrasound beam and the laser or light beam by selective rotation of the motor shaft. The features of this embodiment include the fact that the ultrasound beam and the light beam can focus on the small region of the target tissue at the same time while the MEMS motor 66 is rotating to reflect the two beams.

Figure 9:
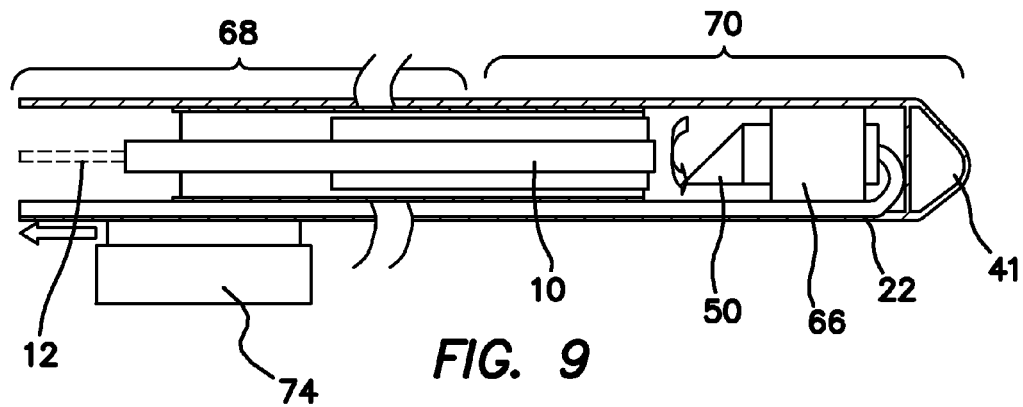
FIG. 9 is a side cross-sectional view of the embodiment of FIG. 8 showing more detail and the use of a linear transversal stage.

FIG. 9 is a side cross-sectional view of a schematic diagram of the embodiment with more details. The proximal portion 68, which is hollow and which contains flexible optical fiber 12, is arranged and configured to be substantially flexible to adapt the probe to practical endovascular use, while distal portion 70 is the only rigid portion and typically is 2.5 cm or less in length. Motor 66 and transducer 52 are provided with power and control signals by means of wire 72 disposed along or in the longitudinal wall of transparent FEP tube 22, which wire 72 is coupled to source of power (not shown) at the proximal end of probe 30. A linear transversal stage 74 is coupled to proximal portion 68 to provide controlled selective longitudinal movement of probe 30. Motor 66 independently provides selectively controlled rotational movement or scanning of probe 30. The overall diameter of probe 10 is approximately 0.5 mm while the overall diameter of transducer 52 is 2.0 mm. A guide wire 34 can be attached to the probe tip for intravascular imaging application.

Figure 10A:
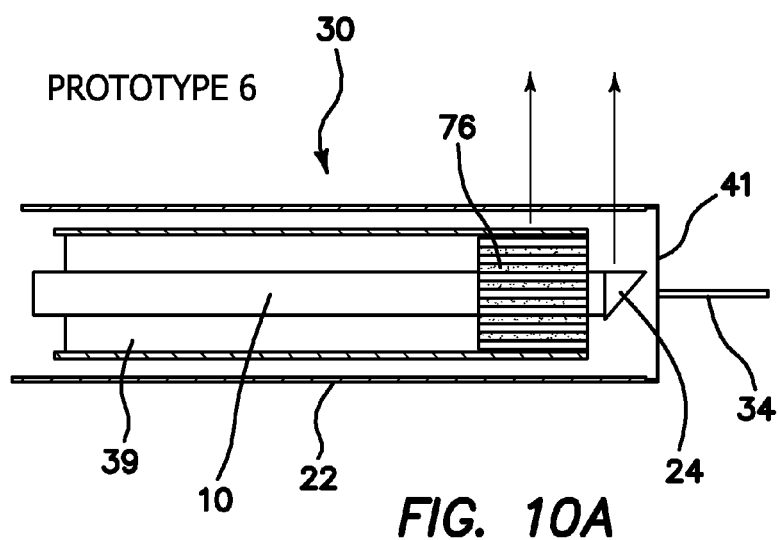
FIG. 10a is a side cross-sectional view of a fifth embodiment of the ultra-OCT imaging probe of the illustrated embodiments using an annular linear array ultrasound probe and the OCT probe of FIG. 1.
Figure 10B:
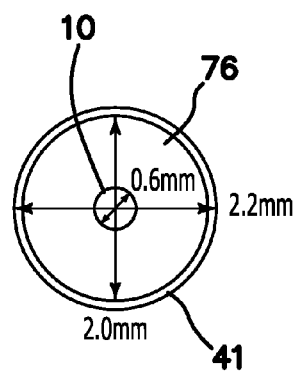

FIG. 10A illustrates another embodiment of the probe 30 made by a conventional annular linear array ultrasound transducer 76 well known to the art such as shown in U.S. Pat. No. 5,520,188 and elsewhere and OCT probe 10. The structure of annular linear array transducer 76 is comprised of an annular or ring array of a plurality of ultrasound transducers, which are arranged into a hollow ring and driven to provide a dynamically focused side beam. OCT probe 10 is disposed through the center, axial opening defined in array 76 as shown in FIG. 10B and reflected by prism 24 into a side beam through transparent FEP tube 22. In this embodiment the overall diameter of probe 10 is approximately 0.6 mm and the overall diameter of transducer 76 is approximately 2.0 mm with the overall diameter of tube 22 within which transducer 76 and probe 10 are embedded or potted is approximately 2.2 mm. Annular linear array ultrasound transducer 76 provides a dynamic focusing depth according to conventional control principles used with annular ultrasound arrays. Mechanical rotation of the probe 30 is required for rotational scanning. A guide wire 34 can be attached to the distal probe tip for the application of intravascular imaging.

Figure 11:
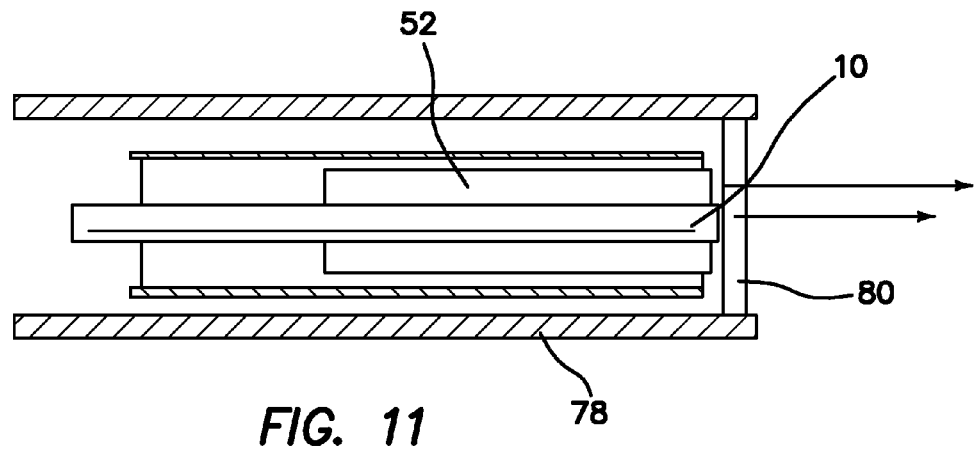
FIG. 11 is a side cross-sectional view of a sixth embodiment of the ultra-OCT imaging probe of the illustrated embodiments using ring-type ultrasound probe and the OCT probe of FIG. 1 adapted for forward scanning.

The embodiments disclosed above are all configure siding-viewing designs. However, it must be expressly understood that forward scanning design can also be realized in for each of the embodiments. FIG. 11 illustrates a schematic of one such forward-viewing ultra-OCT probe 30, wherein a ring-type ultrasound transducer 52 with an axial OCT probe 10 of the type similar to that described in connection with FIGS. 6a, 6b and 7 are disposed within a protective tube 78 capped with a clear or transparent glue covering 80 to provide longitudinal or forward scanning beams. The difference is that no prism is used in this embodiment, thus sound wave from the transducer 52 and focused light beam from the GRIN lens 20 transmit forwardly though the glue 80 and reach biomedical tissue.

Figure 12:
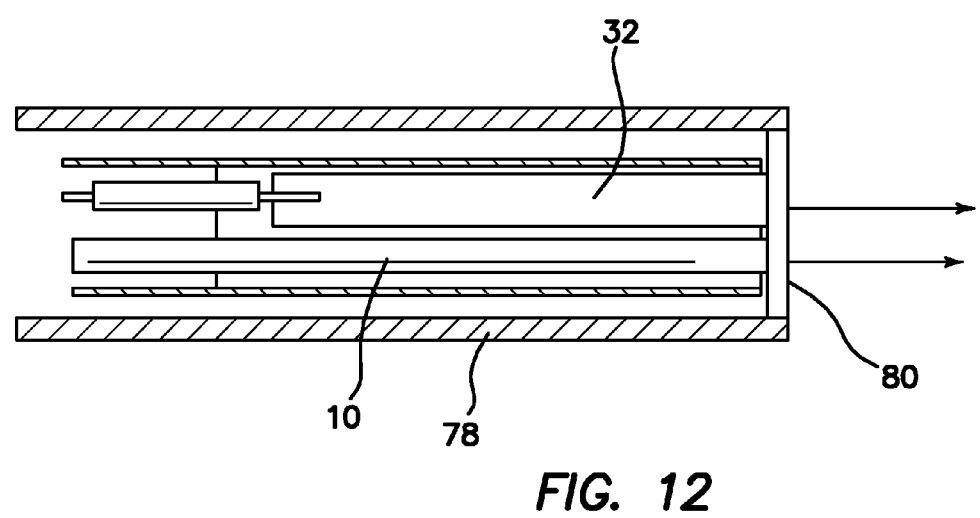
FIG. 12 is a side cross-sectional view of a seventh embodiment of the ultra-OCT imaging probe of the illustrated embodiments using needle ultrasound probe and the OCT probe of FIG. 1 adapted for forward scanning.

Similarly, FIG. 12 illustrates a schematic of another forward-viewing ultra-OCT probe 30, wherein side-by-side ultrasound transducer 32 with an OCT probe 10 of the type similar to that described in connection with FIG. 4 are disposed within a protective tube 78 capped with a clear or transparent glue covering 80 to provide longitudinal or forward scanning beams. In FIG. 12, a needle based transducer 32 and OCT probe 10 are combined together in parallel with the difference being that no prism is used in this embodiment either. Thus sound wave from a needle based transducer 32 and focused light beam from GRIN lens 20 transmit forwardly though the glue 80 and reach biomedical tissue. In all such forward scanning embodiments a PZT based motor or other mechanical method can be adopted to realize longitudinal movement or forward scanning of probe 30.

Thus, it can be appreciated that what is disclosed is a biomedical imaging probe 30 combining intravascular ultrasound (IVUS) and optical coherence tomography (OCT). $Pb(Mg_{1/3}Nb_{2/3})O_3$—$PbTiO_3$ (PMN-PT) needle ultrasound transducers 32, ring type transducer 52, or an annular array transducer 76 with an aperture size of 0.6 mm were fabricated. The measured center frequency and −6 dB fractional bandwidth of the PMN-PT needle ultrasound transducer 32 were 35 MHz and 60% respectively. A mirror 24, 50 was mounted at the tip of the probe at position 45° to change the propagation direction of the ultrasound beam and the laser beam. In vitro images of rabbit trachea and aorta forming from this combined probe have been acquired. These results demonstrate that the complementary nature of these two modalities may yield beneficial results that could not be obtained otherwise.

Figure 13:
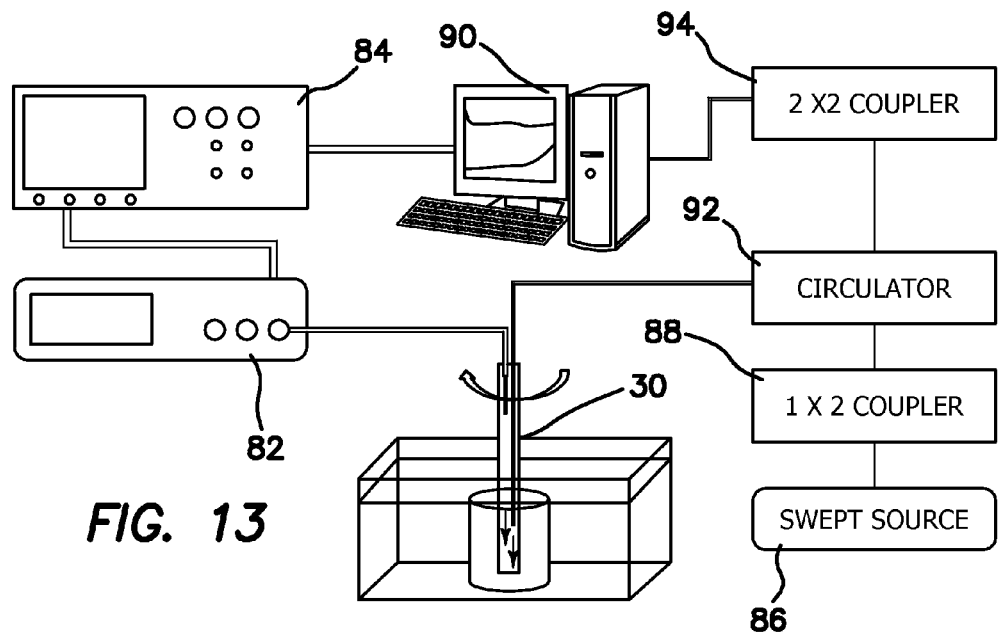
FIG. 13 is a schematic diagram of one embodiment of the imaging system used for data generation, collection, and analysis of the illustrated embodiments of ultra-OCT imaging probe of the illustrated embodiments.

FIG. 13 illustrates one example of a system wherein probe 30 may be utilized. An impedance analyzer (HP 4291B) was used to measure the electrical impedance of the needle ultrasound transducer 32. A pulser/receiver 82 (Panametrics 5900) was used to characterize the needle ultrasound transducer 32. The received echo waveform was displayed on an oscilloscope 84 (LeCroy LC534). The output light from a swept light source 86 (Santec Corporation, Komaki, Aichi, Japan) at 1310 nm with a FWHM bandwidth of 100 nm and output power of 5 mW was split into reference and sample arms by a 1×2 coupler 88 as part of the OCT optical interferometer. The light source 86 was operated at a sweeping rate of 20,000 Hz. Eighty percent of the incident power was coupled into the sample arm while 20% was fed into the reference arm. Mechanically rotating the UltraOCT probe 30 is required to get the intravascular ultrasound image and exciting the ultrasound transducer 32 and collecting the echo signals with 34 dB gain. The received A-mode echo signal was detected, sampled by an eight-bit analog-to-digital converter, converted by scan from a radial ultrasound data format to a rectangular format, and viewed as B-mode images in computer 90. The step angles were chosen by two and four degrees. Therefore, 90 or 180 lines of echo data were used to make an ultrasound image respectively. Circulator 92 and coupler 94 formed optical components of the OCT interferometer coupling ultimately to optical detectors (not shown) and coupled to computer 90. The data collection and analysis for both the ultrasound and OCT signals are conventional and are not further detailed here, but are well known.

Figure 14:
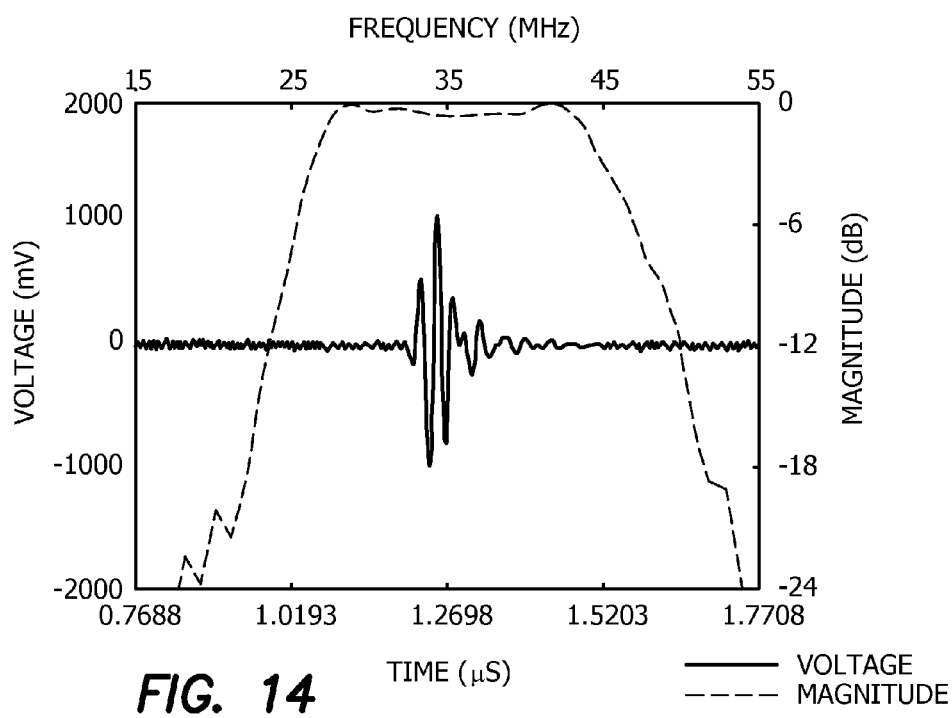
FIG. 14 is a graph of the voltage output of pulse-echo signals of the needle ultrasound probe as a function of time and its frequency spectrum.

FIG. 14 is a graph which shows the measured pulse-echo signals of PMN-PT needle ultrasound transducer 32 and its spectrum. It can be seen that the center frequency of the transducer was approximately 35 MHz. The fractional bandwidth at −6 dB was around 60%. Using the Pulser/Receiver 82 with 1 μJ energy setup, the maximum output voltage (Vpp) of pulse-echo signal was 2.1 V with no gain. These data show that PMN-PT needle ultrasound transducer 32 has a high sensitivity as a result of its excellent piezoelectric properties. It is quite suitable for intravascular ultrasound image applications due to the echo signals of ultrasound from soft tissues are extremely weak.

Figure 15A:
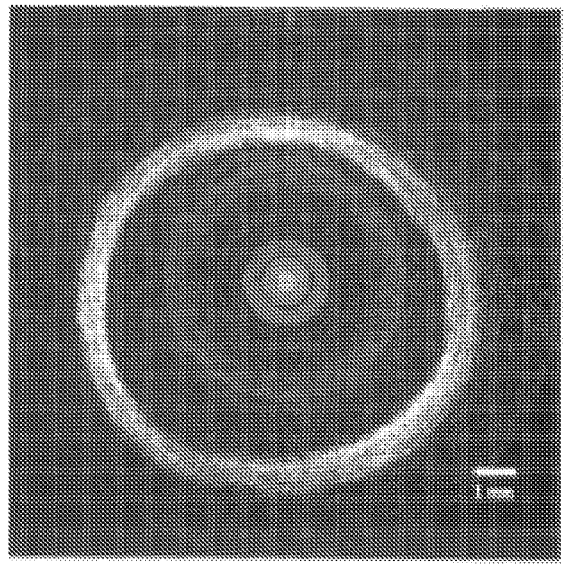
FIGS. 15a and 15b are ultrasound and OCT images respectively of a rabbit aorta taken with the ultra-OCT probe of the invention.
Figure 15B:
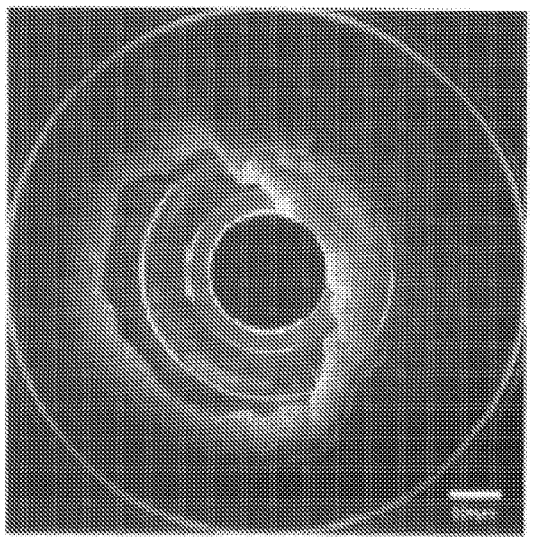

FIG. 15a shows the ultrasound image of rabbit aorta. It is clearly seen that the ultrasound penetrated through the blood vessel forming a cross-sectional image of rabbit aorta. From the cross-sectional image, the average thickness of blood vessel is 1.4 mm can be approximately calculated. The OCT image of the same rabbit aorta is shown for comparison in FIG. 15b. It reveals more detail in the microstructure of the vessel wall. The layered structure around 5 o'clock direction in FIG. 15b is clearly visible.

Figure 16A:
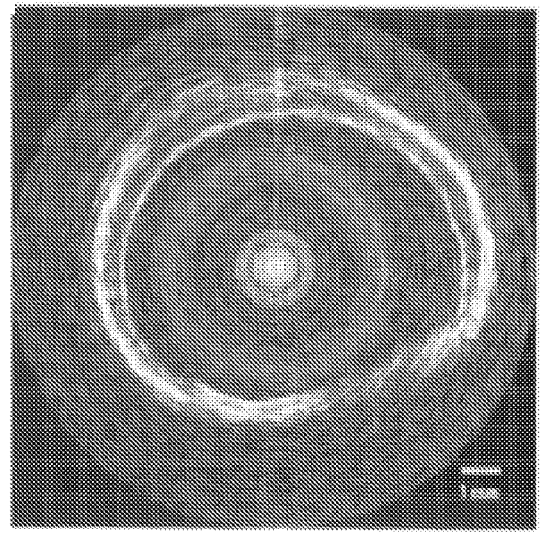
FIGS. 16a and 16b are ultrasound and OCT images respectively of a rabbit trachea taken with the ultra-OCT probe of the invention.
Figure 16B:
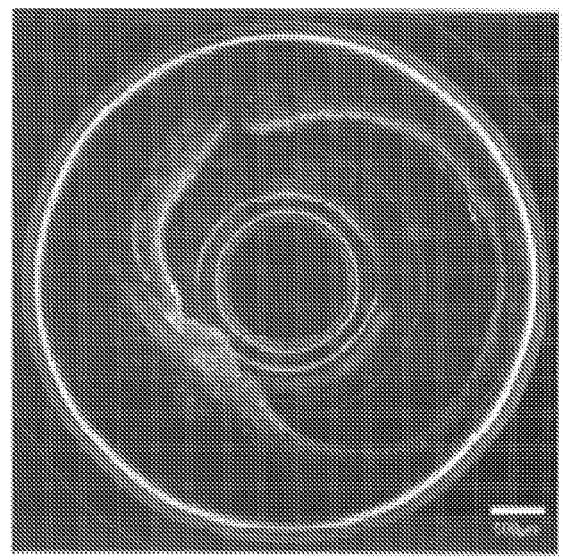

The ultrasound image and OCT image of rabbit trachea are shown in FIGS. 16a and 16b, respectively. FIG. 16a shows the cross-sectional image of trachea of a rabbit. The resolution of FIG. 16a is not as good as FIG. 15a due to fewer lines of echo data. Although, the average thickness of trachea 1.1 mm still can be estimated. From FIG. 16b, the surrounding trachea ring is clearly visible in the left side.

The quality of the images of rabbit aorta and trachea from a 35 MHz PMN-PT needle ultrasound transducer 32 and an OCT probe 10 can be improved by optimizing the design of the UltraOCT probe 30. The disclosed data show that the complementary nature of these two modalities yield beneficial results that could not be obtained otherwise.

Figure 17:
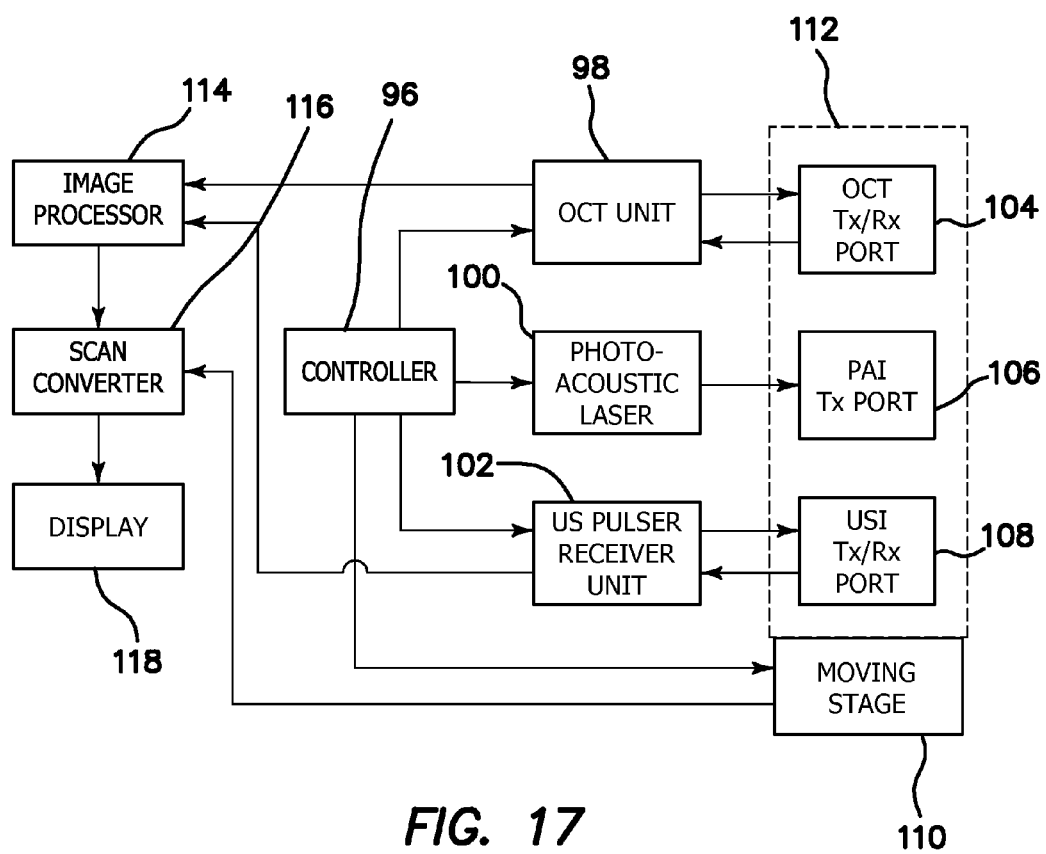
FIG. 17 is a block diagram of a presently preferred embodiment of a multimodality imaging system in accordance with the present invention.

The block diagram, shown in FIG. 17, has a central controller 96 that controls the operation of: OCT unit 98, photoacoustic excitation laser unit 100, and ultrasound pulser/receiver unit 102. An OCT image is acquired through the OCT Tx/Rx port 104; photoacoustic laser 100 excites through the photoacoustics imaging Tx port 106; ultrasound imaging and photoacoustics imaging are both acquired through the ultrasound imaging Tx/Rx port 110. All these ports 104, 106, 108 are integrated into a multimodality image probe, generally denoted by reference numeral 112. Probe 112 is moved in a linear scan mode or a helix scan mode by linear translation stage and microelectromechanical system (MEMS) motor 110 to acquire and construct 2D or 3D tissue cross-sectional imaging.

The OCT, ultrasound imaging, and photoacoustics imaging are further processed at the image processor 114, including noise reduction, filtering, moving average, background reduction, normalization, and image fusion. The processed image contents are remapped through the scan converter 116 to match the image contents to the display coordinates and the data image displayed by display unit 118.

Figure 18:
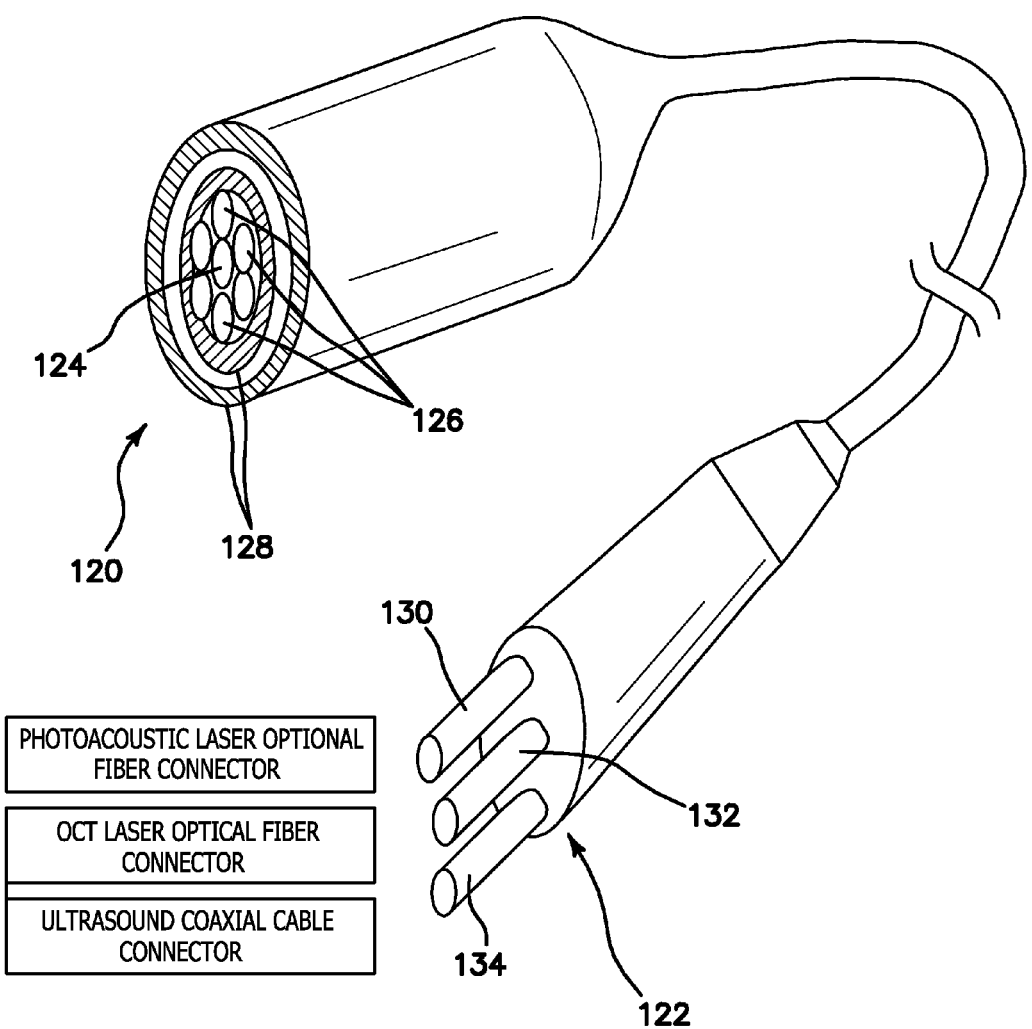
FIG. 18 is general perspective view showing a probe according to this embodiment of the invention, together with a coupling element for connecting optical fibers to the OCT laser/receiving unit and photoacoustic laser unit, and electrical connection to ultrasound pulser/receiver unit. These units are shown in FIG. 17.

FIG. 18 is a perspective diagram of a first embodiment of the image probe 112. Probe 112 has two main ends, one is the image probe head 120, the other is the connector end 122. The image probe head 120 includes: one OCT optical fiber head 124, located at the center of the probe 112, a ring of six multimode optical fibers 126 which deliver photoacoustic excitation laser light, which may suitably be 300-500 micrometers diameter optical fibers, and a double-ring ultrasound transducer 128. The connector end 122 provides connecting ports for a photoacoustic optical fiber connection 130, OCT laser optical fiber connection 132, and ultrasound coaxial cable connection 134. The probe 112 can be held by hand for single point imaging or scanned by a motorized stage (not shown) for 2D or 3D cross-sectional tissue image.

Figure 19A:
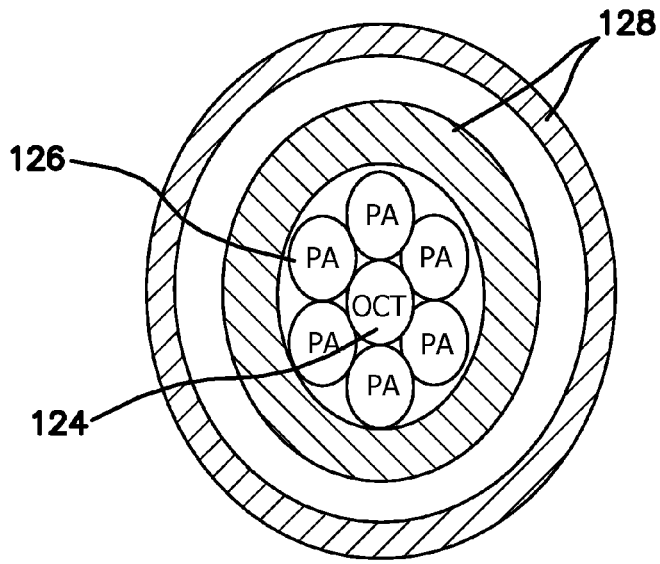
FIGS. 19a and 19b schematically depict the embodiment the probe head arrangement of the invention. It includes: (1) OCT optical head, located at the center of the probe, (2) a circle of photoacoustics imaging excitation optical fibers, and (3) ultrasound double-ring transducers for acquiring ultrasound images and photoacoustics images.
Figure 19B:
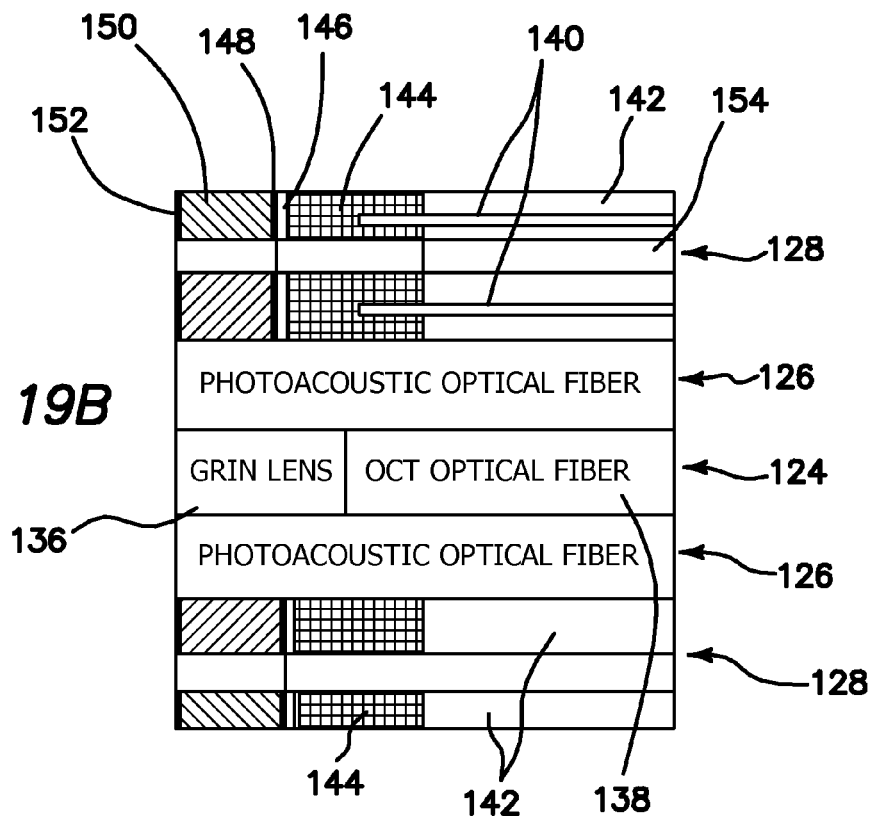

Photoacoustic laser optical fiber connector 130, OCT laser optical fiber connector 132, ultrasound coaxial cable connector 134 and image probe head 120, as shown in FIG. 18, is shown on a larger and detailed scale in FIGS. 19a and 19b. FIG. 19a is a plan end view of the image probe head 120 and FIG. 19b is a cross-sectional view of the structure of the image probe head 120. At the center of the image probe head 120 is a GRIN lens 136 attached to the end of a single mode optical fiber 138 to focus the OCT laser beam from the OCT optical fiber 138. In the illustrated embodiment there are six photoacoustic optical fibers 126 surrounding the OCT optical fiber 138. The number of fibers 126 can be varied according to design choice. These optical fibers 126 transmit photoacoustic excitation laser light into tissues and heat the superficial blood vessels. On the outside of the probe 112, there is a photoacoustic double-ring transducers 128, which is designed for conducting traditional ultrasound imaging of tissues as well as photoacoustics imaging of blood vessels. The cross section of the double-ring transducers 128 show the structure of the active region of the double-ring transducers, including a protective layer made by parylene coating 152, Au electrode 150 for grounding connection, silver-particle front-matching layer 148, piezo-material with Cr/Au electrode 146, silver-particle-back-matching layer 144, conductive epoxy backing 142, electrode conduct wire 140 for each ring 128. There exists an insulation gap 154 between the rings of the double-ring transducer 128.

Figure 20A:
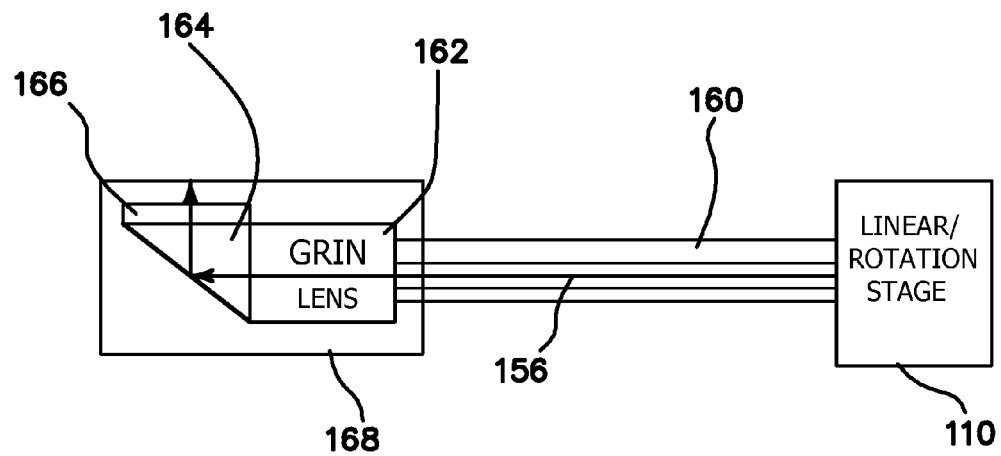
FIGS. 20a and 20b show an embodiment of a side-firing image probe with its side and top view, respectively; the ultrasound transducer is an annular array transducer.
Figure 20B:
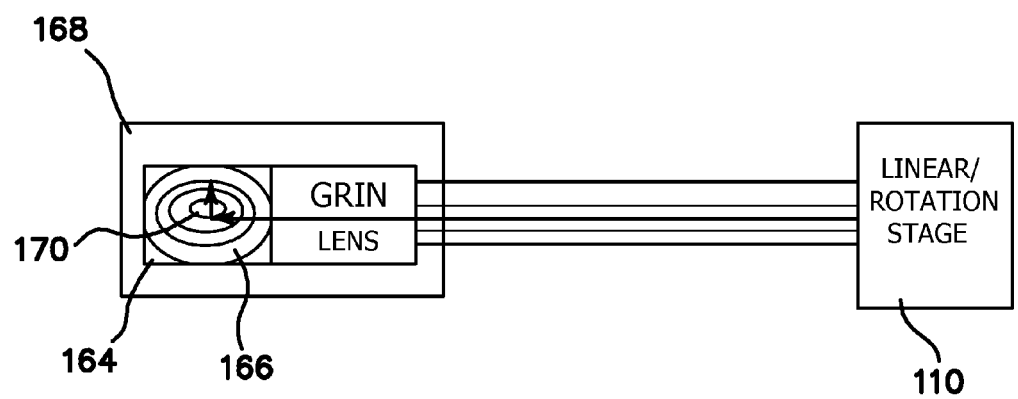

FIG. 20a is a side cross-sectional view of the photoacoustic optical fiber GRIN Lens OCT optical fiber 124, while FIG. 20b is a top cross-sectional view of the same. The integrated image probe 112 in this embodiment is arranged for imaging on its side. FIGS. 20a and 20b show the image probe 112 including a linear/rotation stage 110, a photonic crystal fiber 156 and protection coil sheath 160, GRIN lens 162, reflector 164, annular array ultrasound transducer 166, and glass ferrule 168 filled with acoustic impedance matching oil. GRIN lens 162 is attached to the end of the photonic crystal fiber 156 to collimate and focus continuous NIR laser beam for OCT imaging and nano-second pulsed laser 100 for photoacoustic excitation. Both the continuous and pulsed laser beams are reflected by the reflector 164, and then go through the hole 170 at the center of the annular array ultrasound transducer 166 to acquire OCT image and also to excite blood vessel for acquiring photoacoustics imaging. The image probe 112 is rotated and scanned by the linear/rotation stage 110 to construct 2D and 3D cross-sectional image. Note that photonic crystal fiber 156 is designed to support both single mode and low optical power transmission for OCT applications, and also support multi-mode and higher optical power transmission for photoacoustics imaging applications.

Figure 21:
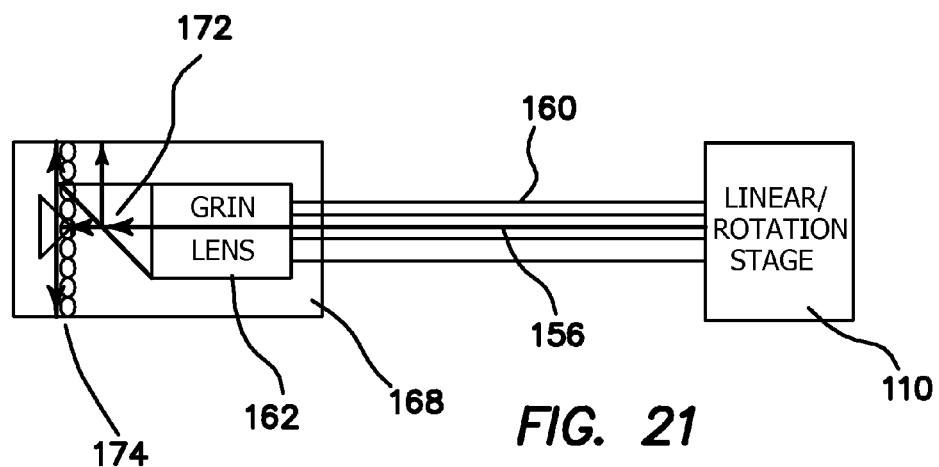
FIG. 21 schematically illustrates another embodiment of a side-firing image probe with phased array transducer.

FIG. 21 shows another embodiment of the side-firing image probe 112 including linear/rotation stage 110, photonic crystal fiber 156 and protection coil sheath 160, GRIN lens 162, dichroic reflector 172, annular array ultrasound transducer 174, and glass ferrule 168 filled with acoustic impedance matching oil. GRIN lens 162 is attached to the end of a photonic crystal fiber 156 to collimate and focus continuous NIR laser beams for OCT imaging. The NIR laser beam for OCT image is reflected by the dichroic reflector 172, while the nano-second pulsed laser for photoacoustic excitation goes through the dichroic reflector 172 and is reflected to generate a ring shape radiation pattern. Photoacoustics imaging is obtained by the phased array ultrasound transducers 174 located in a ring-shape on the probe 112. With this design, a 360 degree photoacoustics image can be obtained by ultrasound using one laser pulse excitation. The rotation stage 110 is used for acquiring 360 degree OCT images. Thus, the image probe 112 can be moved by the linear/rotation stage 110 to obtain and reconstruct 3D cross-sectional images.

The integrated biomedical multimodality image probe 112 can be used to obtain tissue surface and cross-sectional image, from the surface to a few centimeters with superior image resolution, deeper imaging depth, and high contrast in blood vessel imaging. This device has potential applications which include but are not limited to: (a) pre-cancer screening: in gastrointestinal and urogential tracts and on skin; (b) diagnosis and management cardiovascular diseases with intravascular procedures: monitoring aneurysms, stents, atherosclerosis, and plaque build-up; (c) noninvasive blood vessel monitoring such as port wine stain depth and location evaluation, and other blood vessel related tissue imaging and monitoring; (d) tissue perfusion and viability monitoring: determination of burn depth in skin, determination of tissue injury and wound closure, and evaluate blood vessel status; (e) blood vessel imaging: image 3D blood vessel distribution, evaluation of micro-vessel distribution density. (f) monitoring tumor development: monitoring superficial tumor grow and its blood vessel developments, monitoring tumor and its blood vessel reactions to chemotherapy or other tumor therapies.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

Figure 22A:
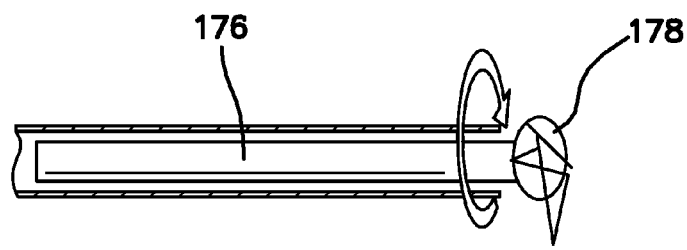
FIGS. 22a and 22b illustrate diagrammatic side cross-sectional view of the side and top view of a lensed optical fiber OCT probe with a ball lens.
Figure 22B:
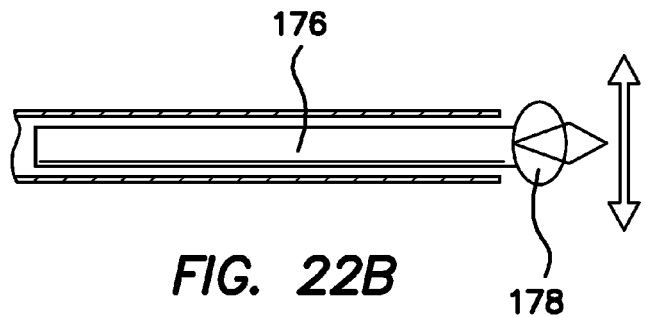

For example, instead of using a GRIN lens and prism for light beam focusing and reflection, a lensed fiber with a 45-degree polished ball lens can also be used to achieve the same purpose. This embodiment of OCT probe 10 uses a lensed fiber 176 with a 45-degree polished ball lens 178 for the purpose of both focusing and reflecting light beam as shown in FIGS. 22a and 22b. A lensed fiber 176 without angle polish can also be used for forward viewing. The lensed fiber OCT probe 10 of FIGS. 22a, 22b can be used to replace the GRIN lens and prism in any one of the embodiments described above.

To reduce the size of the integrated probe 30, a membrane transducer 180 made of flexible thin film piezoelectric materials such as PVDF-TrFE copolymer can be used, as shown in FIGS. 23a and 23b. The thin film transducer 180 can be attached to the OCT probe 10 and provides side-viewing. This embodiment offers decreased overall diameter (<1 mm) of the integrated probe 30, which is preferred when the luminal area of interested organ is small.

The embodiments of FIGS. 22a, 22b, 23a and 23b can be combined in the embodiment of FIGS. 24a and 24b. As shown a lensed fiber with a 45-degree polished ball lens 178 is used in place of the GRIN lens and prism. The single element membrane transducer 180 is attached to optical fiber 176 to provide side-viewing. The integrated OCT lensed fiber and thin film transducer rotates inside of a flexible or rigid housing 182.

The embodiment of FIGS. 25a and 25b uses the same 45-degree polished lensed fiber 176, while a membrane transducer array 184 with multiple elements is attached to the housing outer wall 182 and is stationary when acquiring images. The transducer array 184 is integrated into the inner wall of the outmost tube 182 (not shown), although other methods of embodiment can also be used. Instead of side-viewing, forward viewing can be achieved using a lensed fiber without 45-degree polish. The integration of the lensed fiber OCT probe 10 and membrane transducer 184 further reduces the overall size of the probe 30, which is necessary in the application such as intra-coronary imaging when miniaturization of probe is critical. Instead of lensed fiber OCT probe, a GRIN lens and prism based OCT probe can also be used in these configurations.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An imaging probe for imaging a tissue site comprising:
an integral probe package having a longitudinal axis;
an OCT and/or photoacoustic probe disposed on or parallel to the longitudinal axis of the integral probe package;
a GRIN lens optically coupled to the OCT and/or photoacoustic probe and directed to a corresponding first field of view of the tissue site,
an ultrasound probe having a distal end surface directed to a corresponding second field of view of the tissue site;
where the ultrasound, OCT and/or photoacoustic probe have a common data receiving port;
where the first and second fields of view have an identical view of the tissue site at the same time; and
an image processor electrically coupled to the OCT and/or photoacoustic probe and ultrasound probe, the image processor having a single real time output image taken at one predetermined time from the identical view of the first and second fields of view from the OCT and/or photoacoustic probe and from the ultrasound probe respectively,
whereby a multimodal single image of the tissue site at one predetermined time is produced by the imaging probe.

2. The imaging probe of claim 1 further comprising a flushing port for saline, contrast reagent or a combination thereof, and where the flushing port for saline, contrast reagent or a combination is arranged and configure to allow flushing of the common data receiving port during imaging therethrough.

3. The imaging probe of claim 1 further comprising a reflector disposed in the integral probe package optically coupled to the OCT and/or photoacoustic probe and ultrasound probe, the reflector having an inclined reflecting surface directed to the corresponding first and second fields of view of the tissue site.

4. The imaging probe of claim 1 further comprising a prism optically coupled to the GRIN lens and having an emitting surface directed to the corresponding first field of view of the tissue site and where the ultrasound probe has an inclined transmitting surface directed to the corresponding second field of view of the tissue site.

5. The imaging probe of claim 1 where the ultrasound probe has a longitudinal bore defined therethrough and is disposed along the longitudinal axis of the integral probe package, and has a ring-shaped transducer with an axial bore defined therethrough along the longitudinal axis of the integral probe package, where the OCT and/or photoacoustic probe is disposed concentrically within the longitudinal bore of the ultrasound probe and disposed in the bore defined in the axial bore of the transducer, and further comprising a reflector optically coupled to the OCT and/or photoacoustic probe and ultrasound probe and disposed on the longitudinal axis of the integral probe package, the reflector having an inclined reflecting surface, and ultrasound probe, the inclined reflecting surface directed to the first and second corresponding fields of view of the tissue site.

6. The imaging probe of claim 5 further comprising a motor and where the reflector is mechanically coupled to the motor and rotated thereby.

7. The imaging probe of claim 5 further comprising a linear translator motor and where the reflector and probe are mechanically coupled to the linear translator motor and translated thereby.

8. The imaging probe of claim 5 further comprising a motor mechanically coupled to the integral probe package and rotated thereby.

9. The imaging probe of claim 5 further comprising a linear translator motor mechanically coupled to the integral probe package and translated thereby.

10. The imaging probe of claim 1 where the OCT and/or photoacoustic probe further comprises an optical fiber coupled to the GRIN lens and further comprising a side scanning prism reflector optically coupled to the GRIN lens and directed to the first field of view of the tissue site.

11. The imaging probe of claim 1 where the OCT and/or photoacoustic probe comprises an optical fiber coupled to the GRIN lens, and further comprising a side scanning mirror, and where the ultrasound probe comprises a needle intravascular ultrasound (IVUS) transducer.

12. The imaging probe of claim 1 where the OCT and/or photoacoustic probe have a common optical delivery system and delivers a continuous laser beam through the OCT probe and a pulsed laser beam through the photoacoustic probe through the common optical delivery system.

13. The imaging probe of claim 1 where the OCT and/or photoacoustic probe provides an OCT and/or photoacoustic excitation beam respectively and where the ultrasound probe comprises:
   an optical beam reflector;
   a ring or annular array ultrasound transducer disposed on top of the optical beam reflector; and
   a common optical fiber delivery system optically coupled to the optical beam reflector to deliver the OCT and/or photoacoustic excitation beam through the ring or annular array ultrasound transducer.

14. The imaging probe of claim 1 where the ultrasound probe comprises a side imaging membrane transducer or membrane transducer array coupled to a distal portion of the OCT and/or photoacoustic probe.

15. An in vivo intravascular imaging probe for imaging an in vivo moving intravascular site comprising:
   an in vivo intravascular probe package having a longitudinal axis;
   an OCT and/or photoacoustic probe disposed on or parallel to the longitudinal axis of the in vivo intravascular probe package;
   a GRIN lens optically coupled to the OCT and/or photoacoustic probe and directed to a corresponding first field of view of the in vivo moving intravascular site,
   an ultrasound probe disposed on or parallel to the longitudinal axis of the intravascular probe package, and having a distal end surface directed to a corresponding second field of view of the in vivo moving intravascular site;
   where the first and second fields of view have an identical view of the in vivo moving intravascular site at the same time; and
   an image processor electrically coupled to the OCT and/or photoacoustic probe and ultrasound probe, the image processor having a single real time output image taken at one predetermined time from the identical view of the first and second fields of view from the OCT and/or photoacoustic probe and from the ultrasound probe respectively,
   whereby a multimodal single image of the tissue site at one predetermined time is produced by the in vivo intravascular imaging probe.

\* \* \* \* \*